US009336934B2

(12) United States Patent
Kim et al.

(10) Patent No.: US 9,336,934 B2
(45) Date of Patent: May 10, 2016

(54) METHOD FOR SELECTIVELY ACTIVATING MAGNETIC NANOPARTICLE AND SELECTIVELY ACTIVATED MAGNETIC NANOPARTICLE

(71) Applicant: SEOUL NATIONAL UNIVERSITY R&DB FOUNDATION, Seoul (KR)

(72) Inventors: Sang Koog Kim, Gyeonggi-do (KR); Je Youn Lee, Gyeonggi-do (KR); Ha Youn Lee, Gyeonggi-do (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 0 days.

(21) Appl. No.: 14/415,618

(22) PCT Filed: Sep. 3, 2013

(86) PCT No.: PCT/KR2013/007923
§ 371 (c)(1),
(2) Date: Jan. 19, 2015

(87) PCT Pub. No.: WO2014/038829
PCT Pub. Date: Mar. 13, 2014

(65) Prior Publication Data
US 2015/0213931 A1    Jul. 30, 2015

(30) Foreign Application Priority Data

Sep. 7, 2012   (KR) .................. 10-2012-0099429

(51) Int. Cl.
*H01F 7/00*      (2006.01)
*A61K 9/00*      (2006.01)
*H01F 1/00*      (2006.01)
*A61K 9/50*      (2006.01)
*B82Y 25/00*     (2011.01)

(52) U.S. Cl.
CPC ............ *H01F 7/00* (2013.01); *A61K 9/0009* (2013.01); *A61K 9/5094* (2013.01); *H01F 1/0045* (2013.01); *H01F 1/0054* (2013.01); *B82Y 25/00* (2013.01)

(58) Field of Classification Search
CPC ............ H01F 1/0036–1/0081; A61K 9/5094
USPC ....................................... 335/306
See application file for complete search history.

(56) References Cited

U.S. PATENT DOCUMENTS 5,612,019 A * 3/1997 Gordon ............... A61K 9/5094
                                                424/646
7,731,648 B2   6/2010 Ivkov
(Continued)

FOREIGN PATENT DOCUMENTS

JP  2009-513722 A      4/2009
KR  10-2000-0034772 A  6/2000
KR  10-2003-0008395 A  1/2003
(Continued)

*Primary Examiner* — Ramon M Barrera
(74) *Attorney, Agent, or Firm* — Stuart H. Mayer; Mayer & Williams PC (57) ABSTRACT

Provided is a method of selective activation for a magnetic nanoparticle having a magnetic vortex structure. The method of selective activation for a magnetic nanoparticle in accordance with an embodiment of the present disclosure includes providing a magnetic nanoparticle having a magnetic vortex structure; applying a first magnetic field to the magnetic nanoparticle so that the magnetic nanoparticle has a resonance frequency; and activating the magnetic nanoparticle by applying a second magnetic field having the resonance frequency to the magnetic nanoparticle.

13 Claims, 11 Drawing Sheets

(56) References Cited

U.S. PATENT DOCUMENTS

2010/0259259 A1* 10/2010 Zahn .................. G01R 33/5601
324/309
2010/0303716 A1* 12/2010 Jin .................... A61M 37/0092
424/1.11

FOREIGN PATENT DOCUMENTS

| | | |
|---|---|---|
| KR | 10-2004-0092969 A | 11/2004 |
| KR | 1020060041629 A | 5/2006 |
| KR | 1020060068119 A | 6/2006 |
| KR | 1020060110579 A | 10/2006 |
| KR | 1020090076197 A | 7/2009 |
| KR | 1020090118605 A | 11/2009 |
| KR | 1020100110005 A | 10/2010 |
| KR | 1020120030986 A | 3/2012 |
| KR | 101133054 B1 | 4/2012 |
| KR | 101244193 B1 | 3/2013 |
| KR | 1020130039143 A | 4/2013 |

* cited by examiner

FIG. 14B (b) D=30nm, f=281MHz

FIG. 14C

FIG. 14D (d) D=80nm, f=281MHz

FIG. 15

METHOD FOR SELECTIVELY ACTIVATING MAGNETIC NANOPARTICLE AND SELECTIVELY ACTIVATED MAGNETIC NANOPARTICLE

TECHNICAL FIELD

The present disclosure relates to an activating method, and more particularly, to a method of selective activation using magnetic properties of a magnetic nanoparticle and a magnetic nanoparticle selectively activated by the method.

BACKGROUND ART

Recently, researches using various types of nanoparticles are being actively conducted in biomedical fields such as cell staining, cell separation, drug delivery system, gene transfer, diagnosis and treatment of disease or disorder, and molecular imaging.

For example, drug delivery technology, which is a technology of treating disease by delivering drug to the affected area directly or indirectly without diffusion of the drug in the body, prevents side effects which may be caused by acting of the drug on healthy areas in the body, and can also significantly reduce the drug dosage as compared with general methods. Particularly, an antitumor agent should have not only an effect on cancer cells but also low toxicity and excellent solubility in order to be used for a clinical trial. Many new drugs ended in failure in a clinical trial during the development thereof because they were lacking in one or more of such requirements. Recently, researches on a drug delivery system are intensively being carried out because the drug delivery system can have a possibility of preventing healthy cells from toxicity, or the like. However, through current technology, it is impossible to operate two or more drugs with a time lag, and thus drug delivery with various drugs combined is impossible.

Therefore, to operate two or more drugs at an affected area with a time lag or at different affected parts simultaneously, development of drug delivery system and a bio-applicable magnetic particle which are capable of selectively operating is urgent.

PRIOR ART LITERATURE

Patent Literature

1. KR Patent No. 10-0932613 (registered on Dec. 9, 2009)
2. KR Patent No. 10-0862973 (registered on Oct. 6, 2008)
3. KR Patent No. 10-0848932 (registered on Jul. 22, 2008)

DISCLOSURE OF THE INVENTION

Technical Problem

The present disclosure provides a method of selective activation for a magnetic nanoparticle having a magnetic vortex structure.

The present disclosure also provides a magnetic nanoparticle which is selectively activated by the method and has a magnetic vortex structure.

However, the present disclosure is for illustrative purposes only, and the technical idea of the present invention is not limited thereto.

Technical Solution

In accordance with an embodiment, a method of selective activation for a magnetic nanoparticle includes providing a magnetic nanoparticle having a magnetic vortex structure; applying a first magnetic field to the magnetic nanoparticle so that the magnetic nanoparticle has a resonance frequency; and activating the magnetic nanoparticle by applying a second magnetic field having the resonance frequency to the magnetic nanoparticle.

The first magnetic field may be a DC magnetic field.

The first magnetic field may be applied in the same direction as a magnetic vortex core of the magnetic nanoparticle.

The second magnetic field may be an AC magnetic field or a pulse field.

The second magnetic field may be applied in a direction having a predetermined angle with respect to a direction in which the first magnetic field is applied.

The resonance frequency of the magnetic nanoparticle may vary according to the magnitude of the first magnetic field.

The resonance frequency of the magnetic nanoparticle may vary according to the size of the magnetic nanoparticle.

The magnetic nanoparticle may have a diameter in a range of 40 nm to 200 nm

The magnetic nanoparticle may include at least any one of Permalloy ($Ni_{80}Fe_{20}$), Maghemite ($\gamma$-$Fe_2O_3$), Magnetite ($\gamma$-$Fe_3O_4$), Barium Ferrite ($Ba_xFe_yO_z$; x, y and z are arbitrary) and $CoFe_2O_4$.

In accordance with another embodiment, a method of selective activation for a magnetic nanoparticle includes providing a first magnetic nanoparticle and a second magnetic nanoparticle, each having a magnetic vortex structure; applying a first magnetic field to the first and second magnetic nanoparticles so that the first magnetic nanoparticle has a first resonance frequency and the second magnetic nanoparticle has a second resonance frequency that is different from the first resonance frequency; and selectively activating the first magnetic nanoparticle by applying a second magnetic field having the first resonance frequency to the first and second magnetic nanoparticles.

The method may further include selectively activating the second magnetic nanoparticle by applying a third magnetic field having the second resonance frequency to the first and second magnetic nanoparticles.

In accordance with yet another embodiment, a magnetic nanoparticle is selectively activated by the aforementioned methods of selective activation and has a magnetic vortex structure, wherein the resonance frequency divided by an external magnetic field may vary according to its own size.

Advantageous Effects

A method of selective activation for a magnetic nanoparticle in accordance with the inventive concept can selectively activate a magnetic nanoparticle having a magnetic vortex structure by applying an external magnetic field having corresponding resonance frequency. Such a method of selective activation for a magnetic nanoparticle can be applied to a contrast medium, a drug delivery system, a medicine for thermotherapy, a temperature sensor, and the like.

A method of selective activation for a magnetic nanoparticle in accordance with the inventive concept can induce a magnetic nanoparticle to move toward an affected area and specify the position of the magnetic nanoparticle using magnetic particle imaging (MPI) apparatus or the like. Furthermore, thermotherapy, imaging (MPI), diagnosis, drug delivery, gene transfer, and the like can be carried out by applying a magnetic field having a resonance frequency and then activating a magnetic nanoparticle.

When the method of selective activation for a magnetic nanoparticle in accordance with the inventive concept is used"

for a drug delivery system or a medicine for thermotherapy, it is possible to deliver drugs to a specific organ of the body without a special tagged molecule and control drugs to be selectively released at a specific organ through dissolution of the drug delivery system by a specific frequency by preparing a contrast medium to include a magnetic nanoparticle with various sizes and injecting the contrast medium into the body, thereafter applying an external magnetic field having a resonance frequency which is able to selectively activate only a magnetic nanoparticle with a corresponding size to a desired target organ of the body according to the size of the contrast medium.

The aforementioned effects of the present invention are for illustrative purposes only and the scope of the present invention is not limited thereto.

BRIEF DESCRIPTION OF THE DRAWINGS

Embodiments can be understood in more detail from the following description taken in conjunction with the accompanying drawings, in which.

BEST MODE FOR THE INVENTION

Hereinafter, specific embodiments will be described in detail with reference to the accompanying drawings. Embodiments of the present disclosure are provided to fully describe the inventive concept to those of ordinary skill in the art, embodiments mentioned below may be changed in many different forms, and the scope of the inventive concept is not limited to the embodiments mentioned below. Rather, these embodiments are provided so that this disclosure will be thorough and complete, and will fully convey the inventive concept to those skilled in the art. As used herein, the term "and/or" includes any one and all combinations of one or more of the associated listed items. Like reference numerals or symbols refer to like components or elements throughout. Moreover, various elements and areas in the drawings are schematically illustrated. Therefore, the inventive concept is not limited to relative sizes or distances illustrated in the accompanying drawings.

Figure 1:
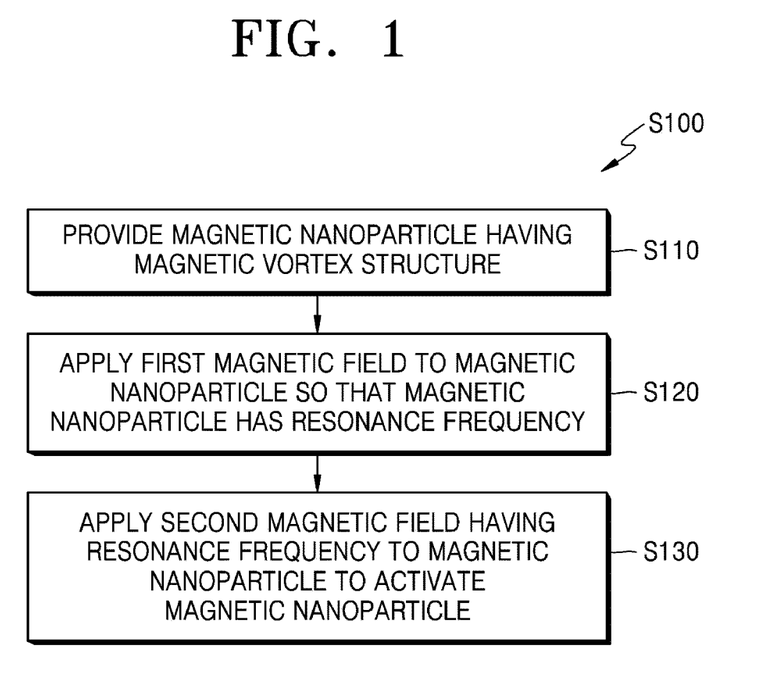
FIG. 1 is a flowchart illustrating a method (S100) of selective activation for a magnetic nanoparticle in accordance with an embodiment.

FIG. 1 is a flowchart illustrating a method (S100) of selective activation for a magnetic nanoparticle in accordance with an embodiment.

With reference to FIG. 1, the method (S100) for selective activation for a magnetic nanoparticle includes providing a magnetic nanoparticle having a magnetic vortex structure (S110); applying a first magnetic field to the magnetic nanoparticle so that the magnetic nanoparticle has a resonance frequency (S120); and applying a second magnetic field having the resonance frequency to the magnetic nanoparticle to activate the magnetic nanoparticle (S130).

The first magnetic field may be a DC magnetic field. The DC magnetic field may be in such a range that a magnetic vortex structure of the magnetic nanoparticle is not changed. For example, in the case where the magnetic nanoparticle is spherical Permalloy ($Ni_{80}Fe_{20}$), the DC magnetic field may be in the range of a few of Oe to a few hundreds of Oe, such as 10 Oe to 300 Oe. However, the shape and material of such a magnetic nanoparticle and the range of the DC magnetic field are exemplarily illustrated, and thus the inventive concept is not limited to thereto. For example, when the size of the magnetic nanoparticle increases, the allowable magnitude of the first magnetic field may increase. These will be described later in detail with reference to FIG. 10.

Furthermore, the first magnetic field may be applied in the same direction of a magnetic vortex core (120, see FIG. 3) of the magnetic nanoparticle.

The second magnetic field may be an AC magnetic field or a pulse field. The second magnetic field may be applied in a direction having a predetermined angle with respect to a direction in which the first magnetic field is applied, and the direction may be perpendicular.

The magnetic nanoparticle may have such a size range that the magnetic nanoparticle has a magnetic vortex structure. For example, in the case of spherical Permalloy ($Ni_{80}Fe_{20}$), the magnetic nanoparticle may be a spherical body having a diameter in the range of dozens of nm to a few hundreds of nm, for instance, in the range of 40 nm to 200 nm. However, the size and shape of the magnetic nanoparticle are for illustrative purposes only, and thus other shapes than the spherical shape or a diameter greater than 200 nm also fall within in the inventive concept.

The magnetic nanoparticle may include a metal, such as iron, cobalt, nickel, or alloys thereof. The magnetic nanoparticle may be, for example, Permalloy ($Ni_{80}Fe_{20}$), Maghemite ($\gamma$-$Fe_2O_3$), Magnetite ($\gamma$-$Fe_3O_4$), Barium Ferrite ($Ba_xFe_yO_z$; x, y, z are arbitrary) and $CoFe_2O_4$ and the like. However, the size, shape, and material of such a magnetic nanoparticle are exemplarily illustrated, and thus the inventive concept is not limited thereto.

The resonance frequency of the magnetic nanoparticle may vary according to the magnitude of the first magnetic field. For example, as the magnitude of the first magnetic field applied to the magnetic nanoparticle increases, the resonance frequency of the magnetic nanoparticle may increase.

Furthermore, the resonance frequency of the magnetic nanoparticle may vary according to the size of the magnetic nanoparticle. For example, as the diameter of the magnetic nanoparticle increases, the resonance frequency of the magnetic nanoparticle may be reduced. Changes in the resonance frequency of the magnetic nanoparticle are shown in Table 1 and Table 2.

Also, the resonance frequency of the magnetic nanoparticle may vary according to the material, size, and/or shape of the magnetic nanoparticle.

Figure 2:
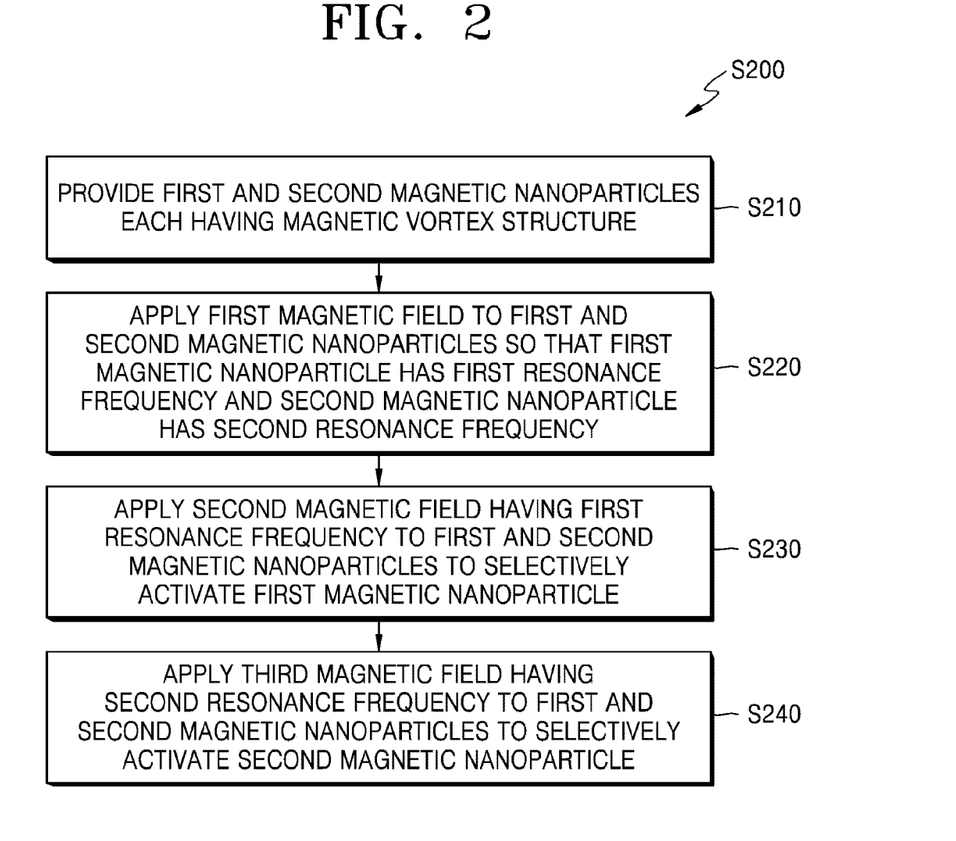
FIG. 2 is a flowchart illustrating a method (S200) of selective activation for a magnetic nanoparticle in accordance with an embodiment.

FIG. 2 is a flowchart illustrating a method (S200) of selective activation for a magnetic nanoparticle in accordance with an embodiment.

With reference to FIG. 2, a method (S200) of selective activation for a magnetic nanoparticle includes providing first and second magnetic nanoparticles each of which has a magnetic vortex structure (S210); applying a first magnetic field to the first and second magnetic nanoparticles so that the first magnetic nanoparticle has a first resonance frequency and the second magnetic nanoparticle has a second resonance frequency which is different from the first resonance frequency (S220); and applying a second magnetic field having the first resonance frequency to the first and second magnetic nanoparticles to selectively activate the first magnetic nanoparticle (S230).

Furthermore, the method S200 of selective activation for a magnetic nanoparticle may further include applying a third magnetic field having the second resonance frequency to the first and second magnetic nanoparticles to selectively activate the second magnetic nanoparticle.

Applications of the method of selective activation for a magnetic nanoparticle in accordance with the inventive concept will be exemplarily described later with reference to FIG. 15.

A magnetic nanoparticle in accordance with the inventive concept is activated by the aforementioned methods for selective activation and has a magnetic vortex structure, wherein the resonance frequency divided by an external magnetic field may vary according to its own size.

Hereinafter, in accordance with the inventive concept, a magnetic nanoparticle having a magnetic vortex structure will be described.

When an external magnetic field of predetermined magnitude is externally applied to a magnetic particle having a small size, spins of the magnetic particle are aligned in a direction of the external magnetic field. During such alignment, the magnetic particle performs a precessional motion about an axis in the direction of the external magnetic field. The precessional motion means such a phenomenon that the rotation axis of a rotating body rotates on a certain immobile axis, and when an external magnetic field is applied to an electromagnetic field which is in motion in a central force field, a magnetic moment of angular momentum rotates about an axis in the direction of the external magnetic field. Specifically, the precessional motion means a resonance phenomenon generated between oscillating magnetic fields or electromagnetic waves when energy levels of a particle having a magnetic moment are separated in a static magnetic field, wherein the oscillating magnetic fields or electromagnetic waves have a frequency corresponding to the separated distance.

The frequency of such a precessional motion is expressed by Equation 1.

$$f = L \cdot B \qquad \text{Equation 1}$$

where, f is a frequency and B is the magnitude of a magnetic field.

Until now, "L" value in Equation 1 is a constant of 2.803 MHz/Oe for a material having a single spin, the constant being known as a Lamor frequency. Therefore, a magnetic nanoparticle having a single magnetic domain has the Lamor frequency because it also acts as a huge spin structure.

However, when the size, shape, and/or material of a magnetic nanoparticle are changed, the magnetic nanoparticle does not act as the single magnetic domain so that "L" in Equation 1 is no more a constant, that is, the magnetic nanoparticle does not have the Lamor frequency. Herein, a magnetic nanoparticle which does not have the Lamor frequency is referred to as "a magnetic nanoparticle having a magnetic vortex structure". For example, in the case where a magnetic nanoparticle has a magnetic vortex structure, the magnetic nanoparticle has a resonance frequency changed according to its diameter.

Figure 3:
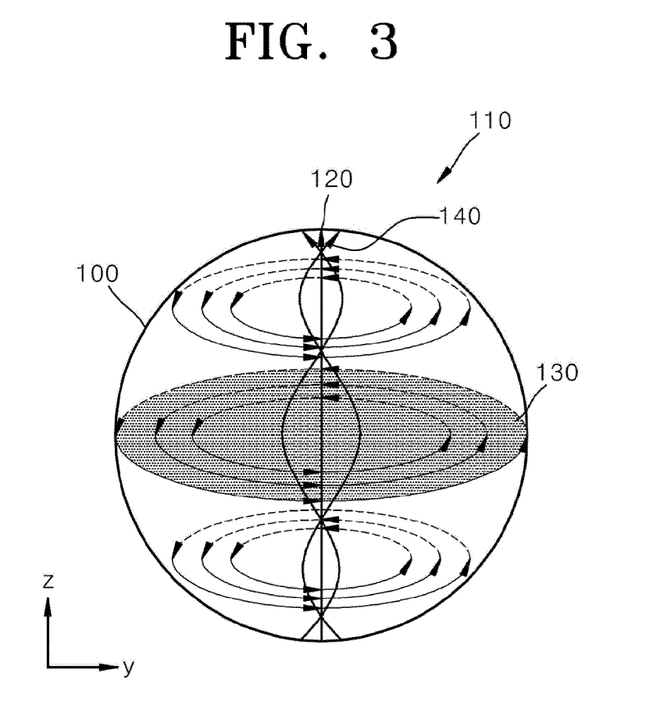
FIG. 3 is a schematic diagram illustrating a magnetic nanoparticle having a magnetic vortex structure in accordance with an embodiment.

FIG. 3 is a schematic diagram illustrating a magnetic nanoparticle 100 having a magnetic vortex structure 110 in accordance with an embodiment.

With reference to FIG. 3, the magnetic nanoparticle 100 may have the magnetic vortex structure 110. The magnetic vortex structure 110 may have a magnetic vortex core component 120, a horizontal magnetization component 130, and a spiral magnetization component 140.

The magnetic vortex core component 120 may penetrate a central portion of the magnetic nanoparticle 100 and a direction of the magnetic force may be +Z direction. The +Z direction may be determined by a direction of a magnetic field which the magnetic nanoparticle 100 has in advance or a direction of an applied external magnetic field.

The horizontal magnetization component 130 may be positioned to rotate clockwise or counterclockwise with an orbit about an axis of the magnetic vortex core 120. The horizontal magnetization component 130 may have various types of orbits, such as a concentric orbit or an elliptical orbit, according to the shape, material, and/or crystal orientation of the magnetic nanoparticle. The horizontal magnetization component 130 may have a predetermined angle with respect to the magnetic vortex core 120, and may be, for example, perpendicular to the magnetic vortex core 120. However, to a certain extent, the horizontal magnetization component 130 may have a magnetization component having a direction of the magnetic vortex core 120 or a magnetization component having a direction opposite to the magnetic vortex core 120, and thus the magnetic vortex core 120 and the horizontal magnetization component 130 may not be perpendicular to each other. The horizontal magnetization component 130 may exist throughout total volume of the magnetic nanoparticle 100.

The spiral magnetization component 140 may be positioned adjacent to the magnetic vortex core 120, and may be directed in the same direction as the magnetic vortex core 120. The spiral magnetization component 140 may be affected by the horizontal magnetization component 130, thereby having a spirally rotating shape. By such a spiral magnetization component 140, a magnetization direction in the magnetic nanoparticle 120 may be gradually changed from the magnetic vortex core 120 to the horizontal magnetization component 130. That is, the magnetization direction in the magnetic nanoparticle 120 may be gradually changed from Z-direction to Y-direction according to an internal position of the magnetic nanoparticle 100.

Figure 4:
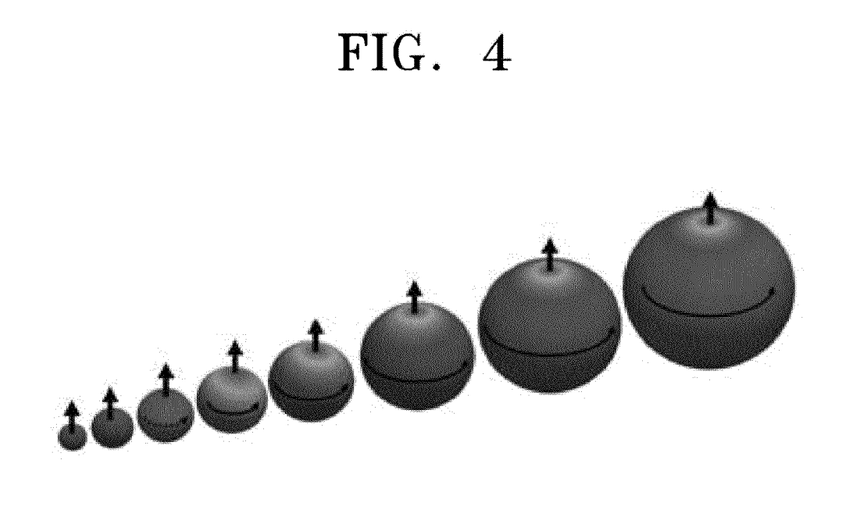
FIG. 4 is a schematic diagram illustrating changes in a magnetic vortex structure according to the size of a magnetic nanoparticle.

FIG. 4 is a schematic diagram illustrating changes in a magnetic vortex structure according to the size of a magnetic nanoparticle.

With reference to FIG. 4, when a magnetic nanoparticle has a small size, magnetization directions are entirely aligned in a direction penetrating a center of the particle (that is, a magnetic vortex core) and the magnetic nanoparticle has a shape of a single magnetic domain. Furthermore, "L" in Equation 1 is a constant of the Lamor frequency in such a case.

Figure 5:
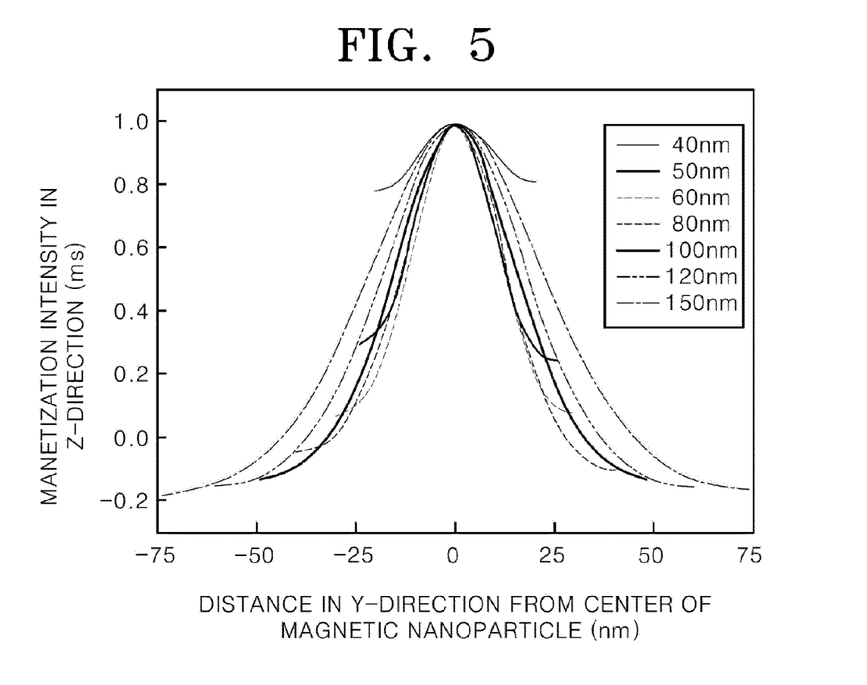
FIG. 5 is a graph showing changes in magnetization intensity in Z-direction versus a distance in Y-direction from the center according to the size of a magnetic nanoparticle.

Alternatively, as the size of a magnetic nanoparticle increases, magnetization at the center of the magnetic nanoparticle is aligned in a direction penetrating the center like a case of the aforementioned single magnetic domain, but surrounding spins spaced from the center are aligned in a circle having a spiral shape with a predetermined angle (for example, perpendicularly) to the central axis. Such a tendency is stronger as the size of a magnetic nanoparticle increases. That is, the magnetic nanoparticle has a magnetic vortex structure, and "L" in Equation 1 has a varying value not a constant of the Lamor frequency. Furthermore, when the shape and/or material of a magnetic nanoparticle is changed, the magnetic nanoparticle may also have a magnetic vortex structure FIG. 5 is a graph showing changes in the intensity of magnetization in Z-direction versus a distance in Y-direction from the center according to the size of a magnetic nanoparticle. Herein, Y-direction and Z-direction are referred to as directions perpendicular to each other.

With the reference to FIG. 5, when a magnetic nanoparticle has a diameter of 40 nm or more, magnetization intensity is further reduced as the distance increases from the center of the magnetic nanoparticle in Y-direction. Although it is not shown, in the case of a magnetic nanoparticle having a small size and a type of a single magnetic domain, such as a magnetic nanoparticle having a diameter of 30 nm or less, central magnetization intensity is not reduced or scarcely reduced even though the distance increases from the center in Y-direction.

In the case of a magnetic nanoparticle having a diameter of 40 nm, magnetization intensity at the surface of the magnetic nanoparticle is reduced as compared with magnetization intensity at the center, but the extent of reduction is not much. Therefore, the magnetic nanoparticle may have a mixed type of a magnetization behavior as a single magnetic domain and a magnetization behavior as a magnetic vortex structure. In the case of a magnetic nanoparticle having a diameter of 50 nm or more, magnetization intensity at the surface of the magnetic nanoparticle reduced by 50% or more as compared with magnetization intensity at the center, and particularly in the case of a magnetic nanoparticle having a diameter of 80 nm or more, magnetization intensity at the surface of the magnetic nanoparticle was found to be zero or less (that is a negative value). Furthermore, the diameter of a magnetic vortex core is also increased as the diameter of a magnetic nanoparticle is increased.

Consequently, in the case of a magnetic nanoparticle having a small size, such as a diameter less than 40 nm, the magnetic nanoparticle shows a magnetization behavior of a single magnetic domain; on the other hand, in the case of a magnetic nanoparticle having a large size, such as a diameter of 40 nm or more, the magnetic nanoparticle shows a magnetization behavior of a magnetic vortex structure.

Figure 6:
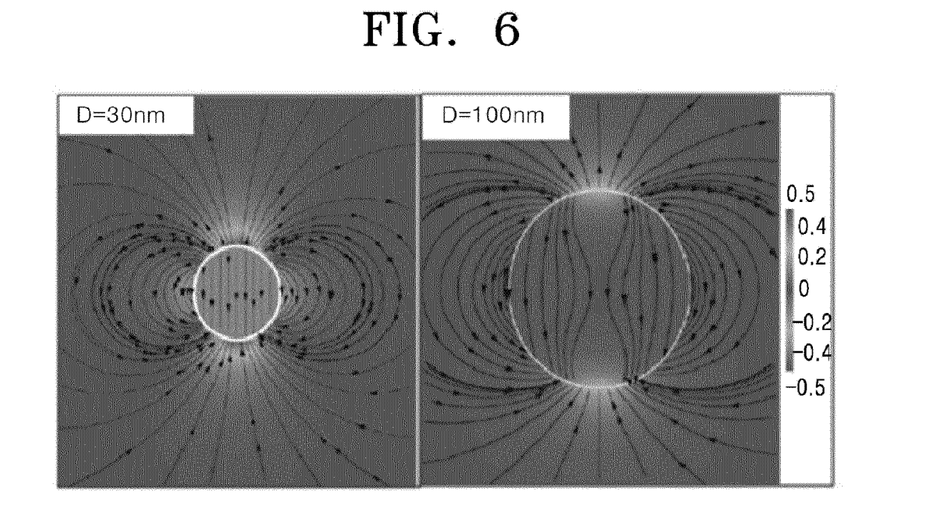
FIG. 6 is a schematic diagram illustrating magnetic fields according to the size of a magnetic nanoparticle.

FIG. 6 is a schematic diagram illustrating magnetic fields according to the size of a magnetic nanoparticle.

With reference to FIG. 6, magnetic fields of a magnetic nanoparticle having a diameter of 30 nm and a magnetic nanoparticle having a diameter of 100 nm are exemplarily illustrated. A magnetic nanoparticle may have a demagnetizing field which is formed inside and a stray magnetic field which flows out of the magnetic nanoparticle. A magnetic nanoparticle having a diameter of 30 nm has a magnetization behavior of a single magnetic domain and a demagnetizing field is generated as a uniform linear fashion. On the other hand, a magnetic nanoparticle having a diameter of 100 nm has a magnetic vortex, a demagnetizing field which is formed inside is generated while being bent so that the demagnetizing field is concentrated to the center. Furthermore, magnetic forces at both poles are relatively large in a magnetic nanoparticle having a diameter of 30 nm as compared with a magnetic nanoparticle having a diameter of 100 nm.

Figure 7:
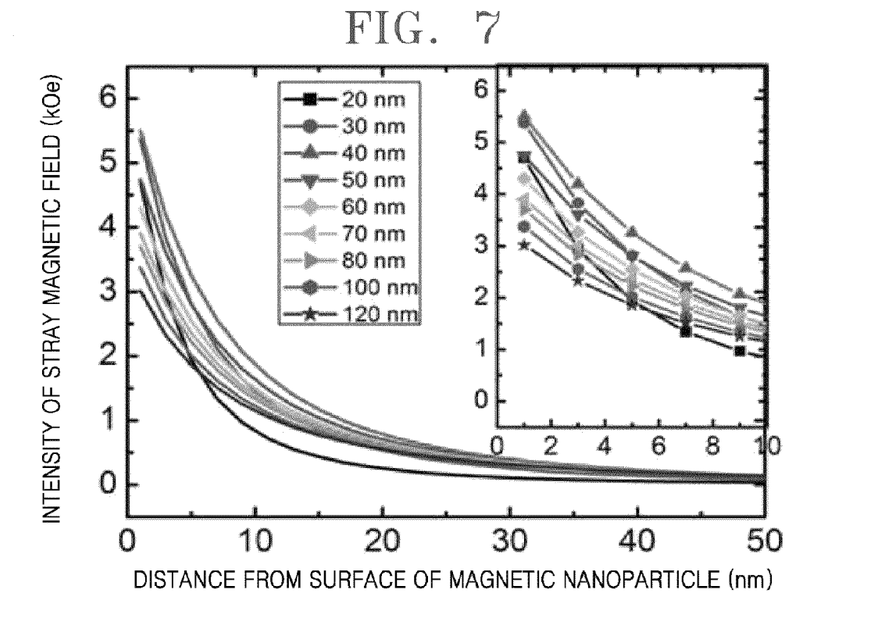
FIG. 7 is a graph showing the intensity of a stray magnetic field versus a distance from a surface of a magnetic nanoparticle according to the size of the magnetic nanoparticle.

FIG. 7 is a graph showing the intensity of a stray magnetic field versus a distance from a surface of a magnetic nanoparticle according to the size of the magnetic nanoparticle.

With reference to FIG. 7, in the case of a magnetic nanoparticle having a diameter of 20 nm to 40 nm, that is, a magnetic nanoparticle having a single magnetic domain structure, the intensity of a stray magnetic field of the magnetic nanoparticle increases as the diameter of the magnetic nanoparticle increases. On the other hand, in the case of a magnetic nanoparticle having a diameter of 40 nm or more, that is, a magnetic nanoparticle having a magnetic vortex structure, the intensity of a stray magnetic field of the magnetic nanoparticle is reduced as the diameter of the magnetic nanoparticle increases.

When the distance from the surface of a magnetic nanoparticle increases, the intensity of a stray magnetic field is reduced in all cases, and the tendency is stronger in the case of a single magnetic domain (that is, in the range of 20 nm to 40 nm) as compared with a magnetic vortex structure (40 nm or more). For example, as compared with a magnetic nanoparticle having a diameter of 30 nm, a magnetic nanoparticle having a diameter of 50 nm shows a lower intensity of a stray magnetic field at the surface of the magnetic nanoparticle, but shows a higher intensity of a stray magnetic field from the distance spaced as much as 4 nm or more from the surface of the magnetic nanoparticle. A magnetic nanoparticle having a diameter of 40 nm is analyzed as a mixed case of a single magnetic domain and a magnetic vortex structure.

Figure 8:
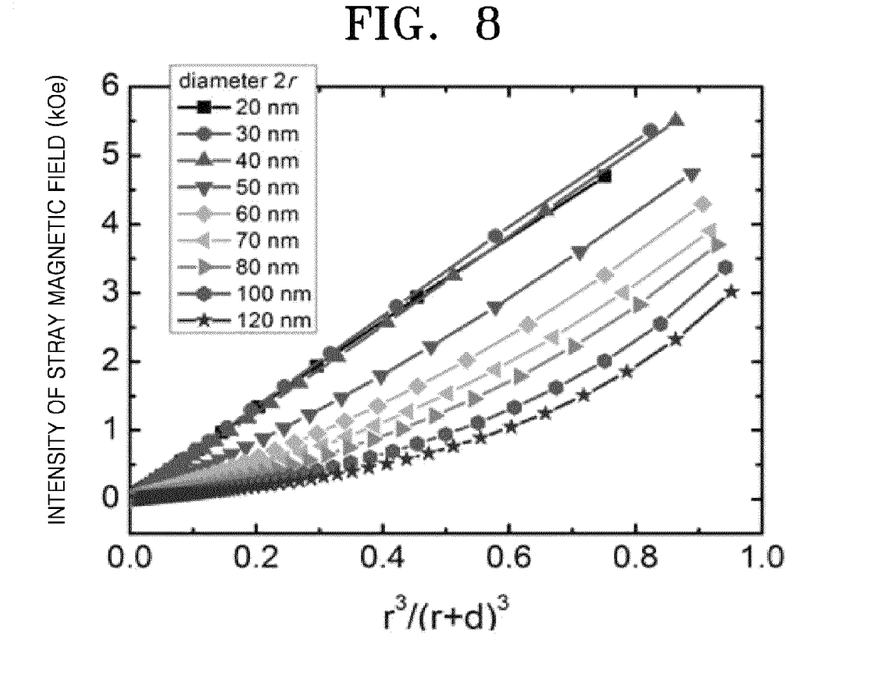
FIG. 8 is a graph showing the intensity of a stray magnetic field versus a normalized distance from a surface of a magnetic nanoparticle according to the size of the magnetic nanoparticle.

FIG. 8 is a graph showing the intensity of a stray magnetic field versus a normalized distance from a surface of a magnetic nanoparticle according to the size of the magnetic nanoparticle.

FIG. 8 is a graph which is normalized the distance from the center of the magnetic nanoparticle as "$1/r^3$" to compare magnitudes of stray magnetic fields released from magnetic nanoparticles having various sizes. That is, there is a relation of $1/(r+d)^3/(1/r^3)=r^3/(r+d)^3$. Herein, "r" means a radius of a magnetic nanoparticle, and "d" means a distance from the surface of a magnetic nanoparticle. FIG. 8 shows the intensity of a stray magnetic field from a point infinitely far away from a magnetic nanoparticle, that is $r^3/(r+d)^3=0$, to a portion in contact with the surface of the magnetic nanoparticle, that is $d=0$ and $r^3/(r+d)^3=1$. In other words, a smaller value of "$r^3/(r+d)^3$" in FIG. 8 means a longer distance from a magnetic nanoparticle.

With reference to FIG. 8, in the case of magnetic nanoparticles having a diameter of 20 nm to 40 nm, the intensity of a stray magnetic field versus a distance from the surface of the magnetic nanoparticle is reduced almost linearly. Such a reduction is the same as a theoretical prediction. That is, in the case of a point dipole which releases a stray magnetic field from a certain point, a theory states that magnetic field intensity at a point in a direction that the stray magnetic field is released is inversely proportional to the third power of a distance from the point, and it is validated. Therefore, it is expected that a stray magnetic field of a magnetic nanoparticle having a single magnetic domain which is deemed to be similar to the point dipole is proportional to "$1/(r+d)^3$". Alternatively, a magnetic nanoparticle having a diameter of 40 nm or more does not show a tendency of the linear reduction any more. Therefore, a magnetic nanoparticle having a magnetic vortex structure does not have a linearly proportional relation and thus the aforementioned theoretical prediction on a single magnetic domain is no more valid.

Figure 9:
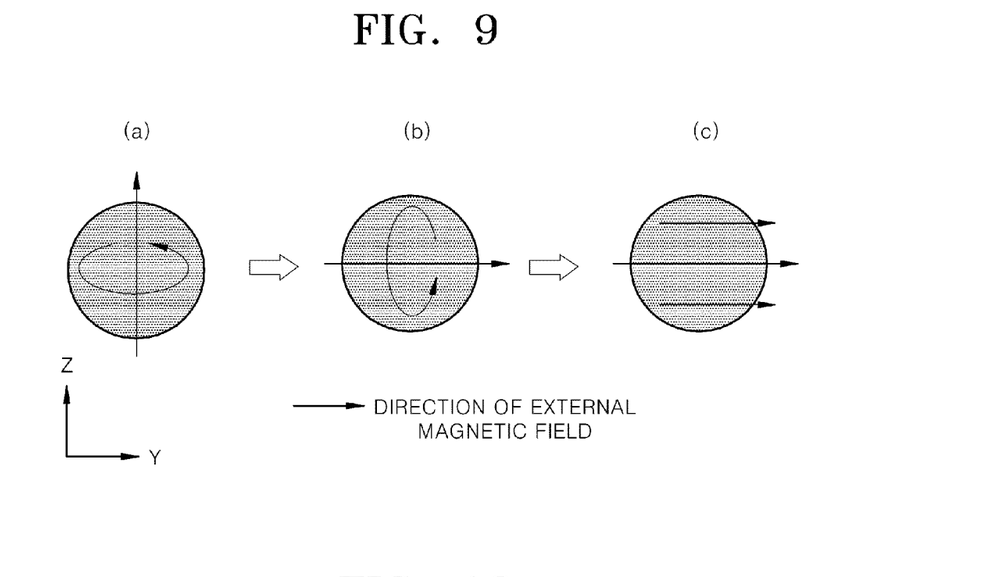
FIG. 9 is a schematic diagram illustrating a magnetization behavior of a magnetic nanoparticle according to an applied external magnetic field.

FIG. 9 is a schematic diagram illustrating a magnetization behavior of a magnetic nanoparticle according to an applied external magnetic field.

With reference to FIG. 9, a magnetic nanoparticle may have a change in a magnetization direction by an external magnetic field. In FIG. 9, +Z direction is used to identify an average magnetization direction, +Y direction is used to identify a direction of an externally applied magnetic field, and the inventive concept is not limited to these directions. Furthermore, +Z direction and +Y direction mean directions different from each other, and they may be perpendicular or not each other.

FIG. 9A is a state before an external magnetic field is applied to a magnetic nanoparticle, and the magnetic nanoparticle may have a magnetization direction in +Z direction. That is, a magnetic vortex core of the magnetic nanoparticle may be directed to +Z direction.

FIG. 9B is a state just after a relatively weak external magnetic field is applied to the magnetic nanoparticle in +Y direction. When a magnetic field is applied to the magnetic nanoparticle in +Y direction which is different from +Z direction which is an average magnetization direction of the magnetic nanoparticle, the magnetic vortex core is directed to +Y direction, and a magnetic vortex is formed around the magnetic vortex core. Subsequently, magnetization is gradually saturated in +Y direction.

FIG. 9C shows the magnetic nanoparticle in which magnetization is saturated in +Y direction when a relatively strong enough external magnetic field is applied to the magnetic nanoparticle.

Alternatively, in the case where a magnetic nanoparticle is a single magnetic domain, magnetization is directed to +Y direction which is a direction of a magnetic field immediately applied by an external magnetic field, and a gradual saturation behavior is not found.

Figure 10:
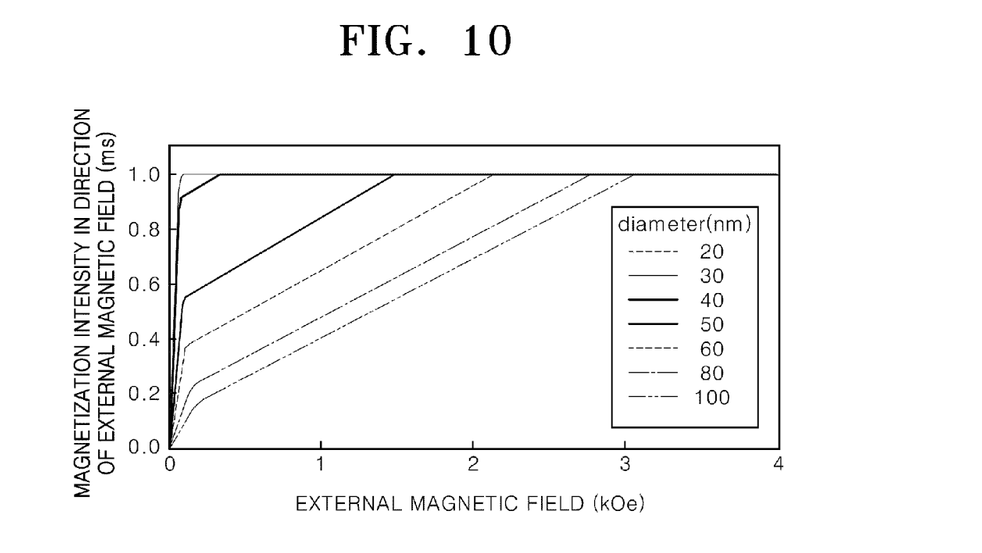
FIG. 10 is a graph showing magnetization intensity of a magnetic nanoparticle in a direction of an external magnetic field versus the external magnetic field according to the size of the magnetic nanoparticle.

FIG. 10 is a graph showing magnetization intensity of a magnetic nanoparticle in a direction of an external magnetic field versus the external magnetic field according to the size of the magnetic nanoparticle.

With reference to FIG. 10, in the case of a magnetic nanoparticle having a diameter of 20 nm to 30 nm, it is shown that magnetization is saturated in the direction of the external magnetic field almost immediately after the external magnetic field is applied. However, in the case of a magnetic nanoparticle having a diameter of 40 nm or more, it can be seen that magnetization is not saturated immediately within a certain magnitude of the external magnetic field. As the diameter of a magnetic nanoparticle increases, the degree of saturation is also reduced and the magnitude of the external magnetic field for saturation increases. For example, in the case of a magnetic nanoparticle having a diameter of 40 nm or more, an external magnetic field of about 350 Oe or more should be applied for saturation, and such a saturation behavior is gradually saturated as described in FIG. 9. If an external magnetic field of 1 Oe to 300 Oe is applied to a magnetic nanoparticle having a diameter of 40 nm or more, magnetization is not saturated and thereby continuing a precession motion by a magnetic vortex structure. Likewise, a magnetic nanoparticle having a magnetic vortex structure has a significantly large value of saturation magnetic field and thus it may be difficult to modify the magnetic vortex structure.

Figure 11:
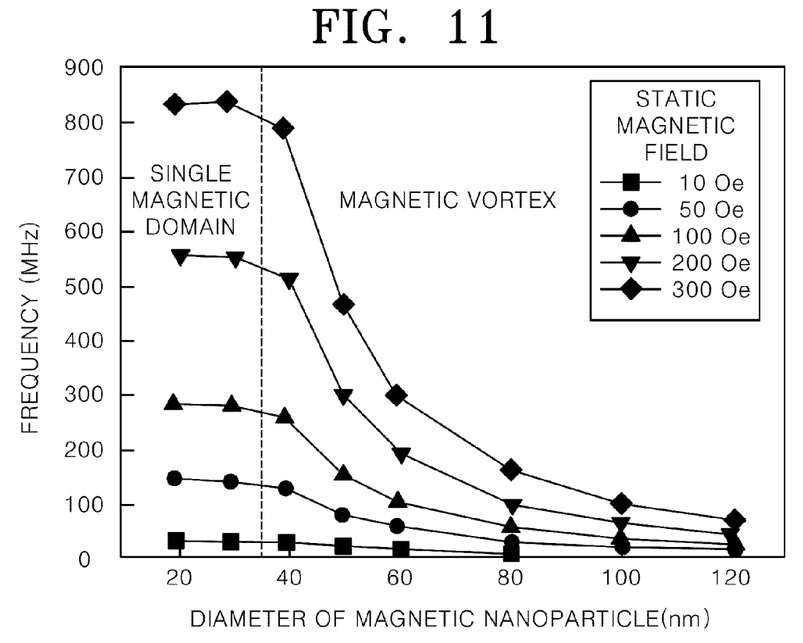
FIG. 11 is a graph showing changes in a resonance frequency according to the size of a magnetic nanoparticle for external static magnetic fields.

FIG. 11 is a graph showing changes in a resonance frequency according to the size of a magnetic nanoparticle for external static magnetic fields.

In FIG. 11, an external static magnetic field applied to a magnetic nanoparticle may be in such a range that a magnetic vortex structure of the magnetic nanoparticle is not changed with reference to FIG. 10, and may be, for example, in the range of 1 Oe to a few hundreds of Oe. However, the external static magnetic field may vary with the diameter of the magnetic nanoparticle.

With reference to FIG. 11, when an external static magnetic field is applied, all spins of a magnetic nanoparticle having a diameter of 20 nm to 30 nm and a single magnetic domain may perform a precession motion about an axis in the direction of the magnetic field of the applied external static magnetic field and thereby being capable of changing the magnetization direction. In this case, a resonance frequency of the magnetic nanoparticle having a diameter of 20 nm to 30 nm (that is, a single magnetic domain) is constantly proportional to the external static magnetic field, and it can be seen that this case is correspond to the case that "L" in the Equation 1 has a constant (2.803 MHz/Oe) of the Lamor frequency.

Alternatively, in the case of a magnetic nanoparticle having a diameter of 40 nm or more and a magnetic vortex structure, a resonance frequency is reduced as the diameter of the magnetic nanoparticle increases. That is, it can be seen that "L" in the Equation 1 has no more a constant of the Lamor frequency while being changed. The reduction ratio of the resonance frequency of a magnetic nanoparticle having a diameter of 40 nm and a magnetic vortex structure drastically increases as the intensity of an external magnetic field increases. Such a reduction in the ratio of a frequency to an external magnetic field according to an increase in the size of a magnetic nanoparticle is confirmed in spherical Permalloy ($Ni_{80}Fe_{20}$).

Figure 12:
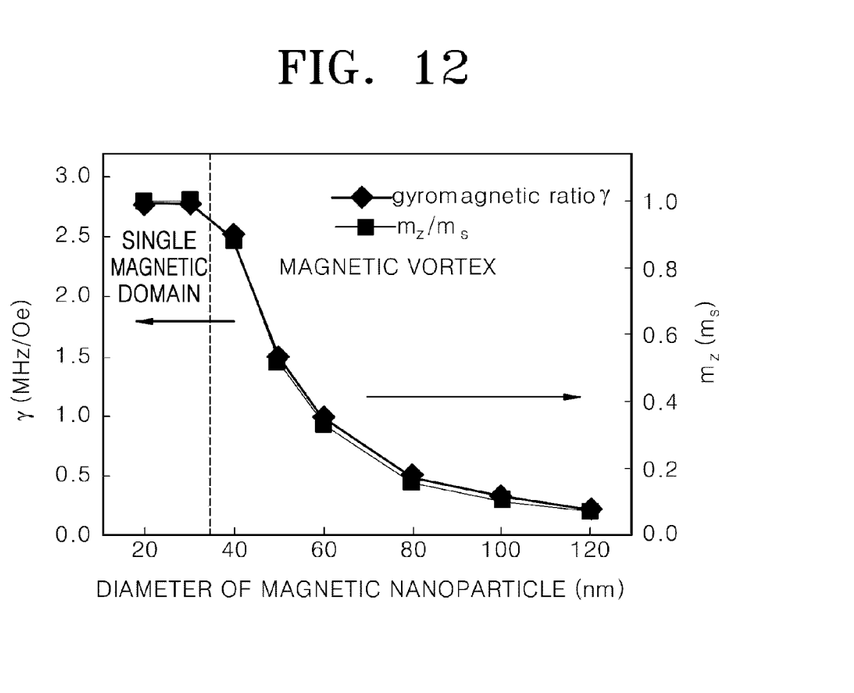
FIG. 12 is a graph showing a gyromagnetic ratio versus the size of a magnetic nanoparticle.

FIG. 12 is a graph showing a gyromagnetic ratio versus the size of a magnetic nanoparticle.

With reference to FIG. 12, a gyromagnetic ratio $\gamma$ of a magnetic nanoparticle is reduced as the size of the magnetic nanoparticle increases. In the case of a single magnetic domain, the gyromagnetic ratio is scarcely reduced. Such change and reduction ratio of a gyromagnetic ratio are correspond to an average magnetic susceptibility ($m_z/m_s$) in a direction of an entire external magnetic field of a magnetic nanoparticle.

Table 1 shows resonance frequencies according to the size of a magnetic nanoparticle and the magnitude of an external static magnetic field. Table 2 shows values of "resonance frequency/external magnetic field" according to the size of a magnetic nanoparticle and the magnitude of an external static magnetic field, wherein the values are obtained with a resolution of 2 MHz.

TABLE 1

|  | 10 Oe | 50 Oe | 100 Oe | 200 Oe | 300 Oe |
| --- | --- | --- | --- | --- | --- |
| 20 nm | 28 MHz | 140 MHz | 280 MHz | 562 MHz | 844 MHz |
| 30 nm | 28 MHz | 140 MHz | 280 MHz | 562 MHz | 844 MHz |
| 40 nm | 24 MHz | 124 MHz | 250 MHz | 516 MHz | 782 MHz |
| 60 nm | 10 MHz | 50 MHz | 98 MHz | 194 MHz | 294 MHz |
| 80 nm | 4 MHz | 24 MHz | 50 MHz | 102 MHz | 156 MHz |
| 100 nm | 2 MHz | 16 MHz | 32 MHz | 64 MHz | 98 MHz |
| 120 nm | 2 MHz | 12 MHz | 22 MHz | 44 MHz | 66 MHz |

TABLE 2

|  | 10 Oe | 50 Oe | 100 Oe | 200 Oe | 300 Oe |
| --- | --- | --- | --- | --- | --- |
| 20 nm | 2.80 MHz/Oe | 2.80 MHz/Oe | 2.80 MHz/Oe | 2.80 MHz/Oe | 2.80 MHz/Oe |
| 30 nm | 2.80 MHz/Oe | 2.80 MHz/Oe | 2.80 MHz/Oe | 2.80 MHz/Oe | 2.80 MHz/Oe |
| 40 nm | 2.40 MHz/Oe | 2.48 MHz/Oe | 2.50 MHz/Oe | 2.58 MHz/Oe | 2.61 MHz/Oe |
| 60 nm | 1.00 MHz/Oe | 1.00 MHz/Oe | 0.98 MHz/Oe | 0.97 MHz/Oe | 0.98 MHz/Oe |
| 80 nm | 0.40 MHz/Oe | 0.48 MHz/Oe | 0.50 MHz/Oe | 0.51 MHz/Oe | 0.52 MHz/Oe |
| 100 nm | 0.20 MHz/Oe | 0.32 MHz/Oe | 0.32 MHz/Oe | 0.32 MHz/Oe | 0.33 MHz/Oe |
| 120 nm | 0.20 MHz/Oe | 0.24 MHz/Oe | 0.22 MHz/Oe | 0.22 MHz/Oe | 0.22 MHz/Oe |

Figure 13:
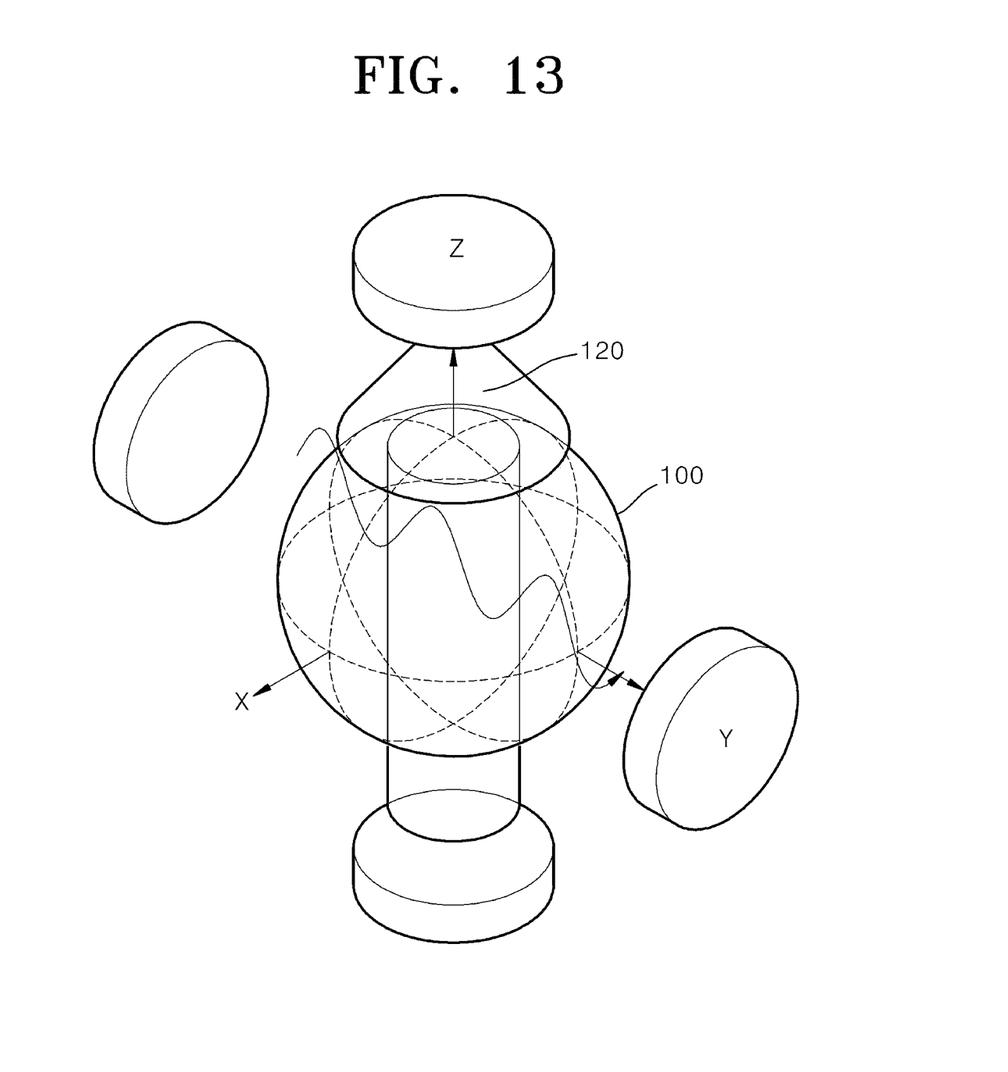
FIG. 13 is a schematic diagram illustrating a method applying a DC magnetic field and an AC magnetic field to a magnetic nanoparticle so as to examine resonance according to a magnetic field applied to the magnetic nanoparticle.

FIG. 13 is a schematic diagram illustrating a method applying a DC magnetic field and an AC magnetic field to a magnetic nanoparticle 100 so as to examine resonance according to a magnetic field applied to the magnetic nanoparticle 100.

With reference to FIG. 13, a DC magnetic field is applied in +Z direction which is a direction of a magnetic vortex core component 120 of a magnetic nanoparticle 100, and an AC magnetic field is applied in a direction different from the +Z direction, such as +Y direction which is perpendicular to the +Z direction. As shown in Table 1, a resonance frequency of a magnetic nanoparticle 100 may be determined according to the diameter of the magnetic nanoparticle 100 and the magnitude of the DC magnetic field. The magnitude of the AC magnetic field may be small as compared with the magnitude of the DC magnetic field, and thus behaviors of the magnetic nanoparticle 100 were observed by changing a frequency of the AC magnetic field.

For example, magnetic nanoparticles having diameters of 30 nm and 80 nm are selected. A DC magnetic field applied in Z-direction is selected to have its magnitude of about 100 Oe. An AC magnetic field applied in Y-direction is selected to have its magnitude of about 10 Oe. Frequencies of the AC magnetic field are selected to be 281 MHz which is a resonance frequency of the magnetic nanoparticle having a diameter of 30 nm, and to be 50 MHz which is a resonance frequency of the magnetic nanoparticle having a diameter of 80 nm.

FIG. 14 is graphs showing resonances of magnetic nanoparticles when AC magnetic fields having different frequencies are applied thereto according to the size of the magnetic nanoparticle.

Figure 14A:
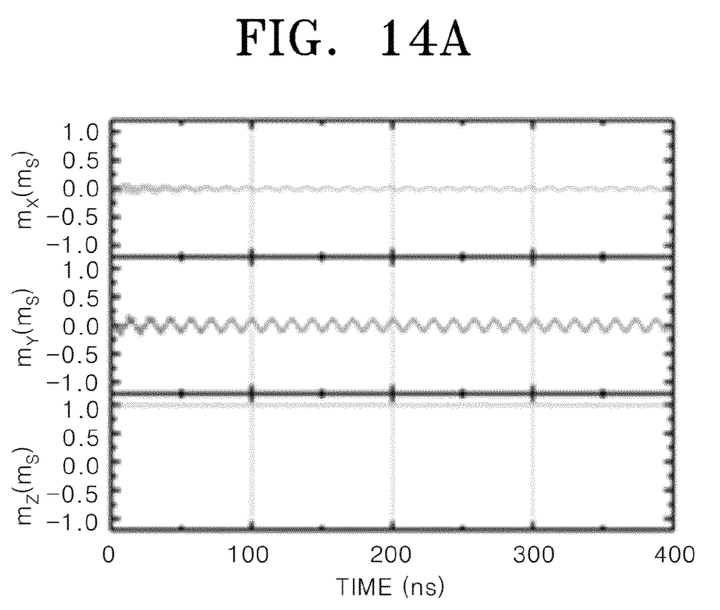
FIG. 14 is graphs showing resonances of magnetic nanoparticles when AC magnetic fields having different frequencies are applied thereto according to the size of the magnetic nanoparticle.
Figure 14B:
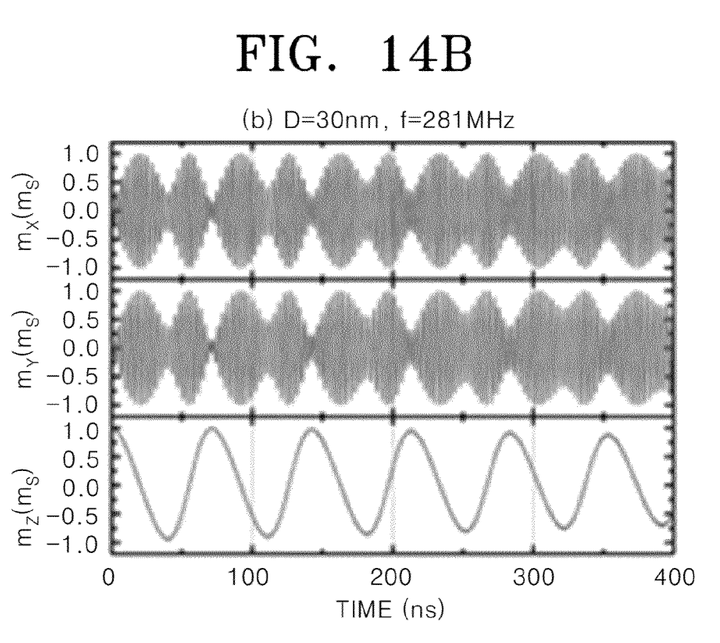
Figure 14C:
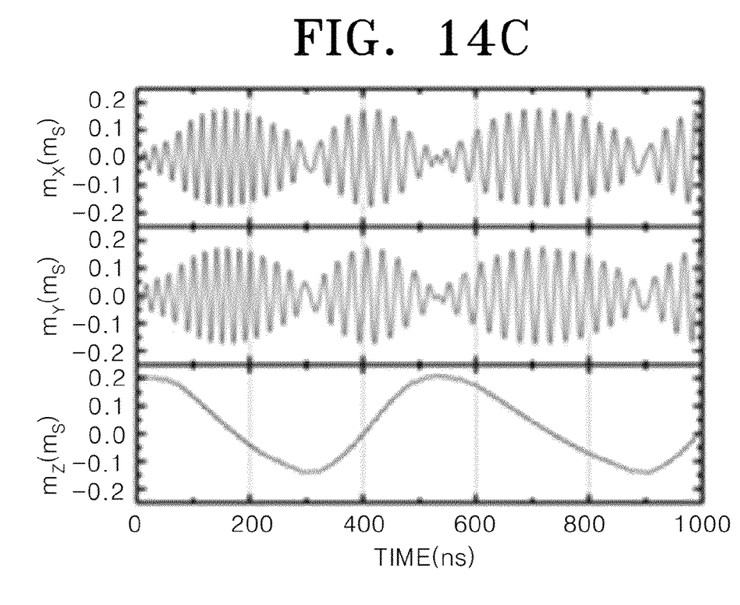
Figure 14D:
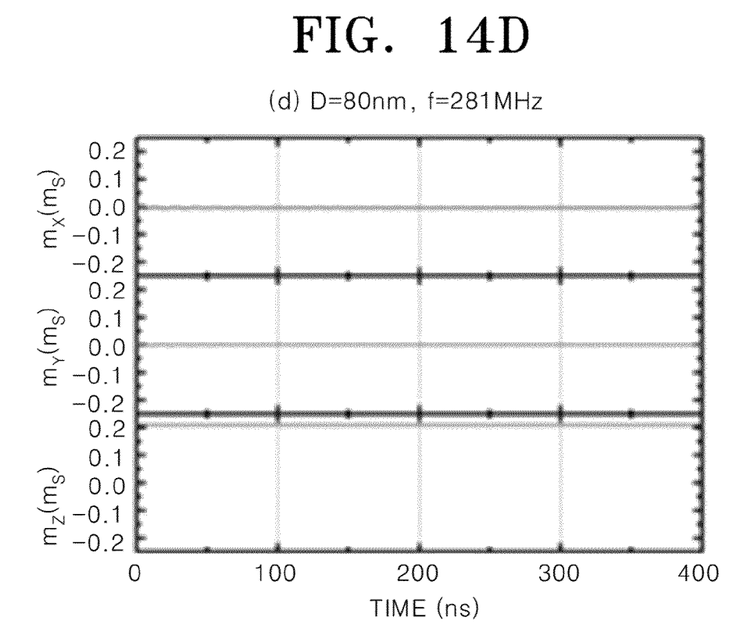

FIGS. 14A and 14B are the case of a magnetic nanoparticle having a diameter of 30 nm. FIGS. 14C and 14D are the case of a magnetic nanoparticle having a diameter of 80 nm.

With reference to FIG. 14, in the case of a magnetic nanoparticle having a diameter of 30 nm, there is no change when an AC magnetic field having a frequency of 50 MHz is applied (refer to FIG. 14A), but when an AC magnetic field having a frequency of 281 MHz which is its own resonance frequency is applied, it is shown that a violent precession motion and other motions, such as magnetization reversal, are active in respond to the applied magnetic field having the resonance frequency (refer to FIG. 14B).

In the case of a magnetic nanoparticle having a diameter of 80 nm, there is no change when an AC magnetic field having a frequency of 281 MHz is applied (refer to FIG. 14D), but when an AC magnetic field having a frequency of 50 MHz which is its own resonance frequency is applied, it is shown that a violent precession motion and other motions, such as magnetization reversal, are active in respond to the applied magnetic field having the resonance frequency (refer to FIG. 14C).

That is, when a magnetic field having a frequency is applied to a magnetic nanoparticle and the frequency is its own resonance frequency, motions, such as a precession motion, become active by the magnetic field, such motions are related to an activation in term of energy, and for example, the magnetic nanoparticle may be heated.

Furthermore, a magnetic nanoparticle having a magnetic vortex structure has different resonance frequencies according to its diameter, and thus the magnetic nanoparticle may be selectively activated according to its diameter for a resonance frequency of an applied magnetic field.

Figure 15:
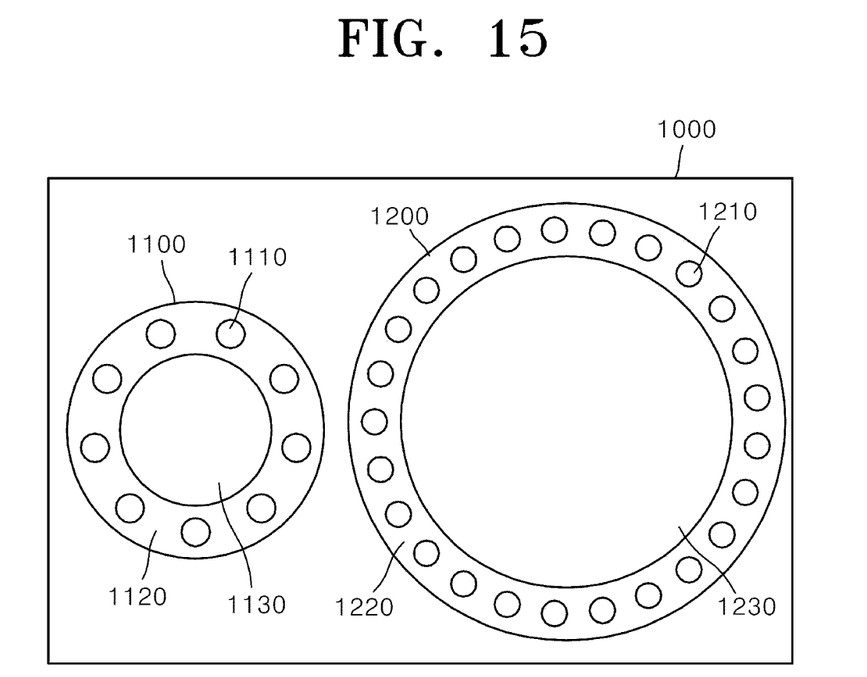
FIG. 15 is a schematic diagram illustrating a drug delivery system using a method of selective activation for a magnetic nanoparticle.

FIG. 15 is a schematic diagram illustrating a drug delivery system 1000 using a method of selective activation for a magnetic nanoparticle.

With reference to FIG. 15, the drug delivery system 1000 may include first and second drug systems 1100 and 1200.

The first drug system 1100 may include a first magnetic nanoparticle 1130 which is positioned inside the first drug system 1100, a first cover 1120 surrounding the first magnetic nanoparticle 1130, and a first drug 1110 which is positioned the first cover 1120.

The second drug system 1200 may include a second magnetic nanoparticle 1230 which is positioned inside the first drug system 1200, a second cover 1220 surrounding the second magnetic nanoparticle 1230, and a second drug 1210 which is positioned the second cover 1220.

The first and second drugs 1110 and 1210 may be different drugs or the same drug. The first and second drugs 1110 and 1210 may not be exposed to the outside.

The first and second covers 1120 and 1220 surround the first and second drugs 1110 and 1210, respectively, while including the first and second drugs 1110 and 1210, respectively, and prevent the first and second drugs 1110 and 1210 from being exposed to the outside, thereby being capable of preventing outflow of the drug. The first and second covers 1120 and 1220 may include a material which is melted by heat. For example, they may include a polymer. The first and second covers 1120 and 1220 may include the same material or different materials.

At least one of the first and second nanoparticles 1130 and 1230 may have a magnetic vortex structure in accordance with the inventive concept. The first and second nanoparticles 1130 and 1230 may have different sizes. The first and second nanoparticles 1130 and 1230 may have different resonance frequencies. The first and second nanoparticles 1130 and 1230 may be selectively activated for external magnetic fields having their own resonance frequencies, thereby being heated and capable of melting the first and second covers 1120 and 1220, respectively. The first and second covers 1120 and 1220 are melted by the first and second nanoparticles 1130 and 1230, respectively, and then the first and second drugs 1110 and 1210 can be injected into the body.

For example, when an external magnetic field corresponding to the resonance frequency of the first magnetic nanoparticle 1130 is applied, the first magnetic nanoparticle 1130 is selectively activated and heated to melt the first cover 1120 so that the first drug 1110 included in the first cover 1120 is injected into the body. However, the second magnetic nanoparticle 1230 is not activated and thus the second drug 1210 is not injected into the body.

Likewise, a drug delivery system including a magnetic nanoparticle having a magnetic vortex structure can selectively delivery two or more different drugs to one affected area, and can reduce side effects according to drug dosage because the drug delivery system can release the same kind of drug with a time lag. Furthermore, the drug delivery system can release different kinds of drugs with a time lag so that it can inhibit side effects due to mutual interaction between different injecting drugs and can efficiently mix two or more drugs if necessary. Furthermore, since penetrability of particle in blood vessel is largely different according to part of body, it is possible to treat simultaneously by injecting magnetic nanoparticles with different sizes simultaneously and then applying external magnetic fields having various frequencies simultaneously or sequentially. Such a therapy method can more effectively treat cancer, a tumor and other kinds of disease and ailment than current methods.

Although the method of selective activation for magnetic nanoparticle and the selectively activated magnetic nanoparticle have been described with reference to the specific embodiments, they are not limited thereto. Therefore, it will be readily understood by those skilled in the art that various modifications and changes can be made thereto without departing from the spirit and scope of the present invention defined by the appended claims.

DESCRIPTIONS OF THE REFERENCE NUMERALS IN THE DRAWINGS

100: Magnetic nanoparticle
110: Magnetic vortex structure
120: Magnetic vortex core component
130: Horizontal magnetization component
140: Spiral magnetization component

The invention claimed is:

1. A method for selectively activating a magnetic nanoparticle, the method comprising:
 providing a magnetic nanoparticle having a magnetic vortex structure;
 applying a first magnetic field to the magnetic nanoparticle so that the magnetic nanoparticle has a resonance frequency; and
 activating the magnetic nanoparticle by applying a second magnetic field having the resonance frequency to the magnetic nanoparticle.

2. The method of claim 1, wherein the first magnetic field is a DC magnetic field.

3. The method of claim 1, wherein the first magnetic field is applied in the same direction as a magnetic vortex core of the magnetic nanoparticle.

4. The method of claim 1, wherein the second magnetic field is an AC magnetic field or a pulse field.

5. The method of claim 1, wherein the second magnetic field is applied in a direction having a predetermined angle with respect to a direction in which the first magnetic field is applied.

6. The method of claim 1, wherein the resonance frequency of the magnetic nanoparticle varies according to the magnitude of the first magnetic field.

7. The method of claim 1, wherein the resonance frequency of the magnetic nanoparticle varies according to the size of the magnetic nanoparticle.

8. The method of claim 1, wherein the magnetic nanoparticle has a diameter in a range of 40 nm to 200 nm.

9. The method of claim 1, wherein the magnetic nanoparticle comprises at least any one of Permalloy ($Ni_{80}Fe_{20}$), Maghemite ($\square$-$Fe_2O_3$), Magnetite ($\square$-$Fe_3O_4$), Barium Ferrite ($Ba_xFe_yO_z$; x, y and z are arbitrary) and $CoFe_2O_4$.

10. A method for selectively activating a magnetic nanoparticle, the method comprising:
 providing a first magnetic nanoparticle and a second magnetic nanoparticle, each having a magnetic vortex structure;
 applying a first magnetic field to the first and second magnetic nanoparticles so that the first magnetic nanoparticle has a first resonance frequency and the second magnetic nanoparticle has a second resonance frequency that is different from the first resonance frequency; and
 selectively activating the first magnetic nanoparticle by applying a second magnetic field having the first resonance frequency to the first and second magnetic nanoparticles.

11. The method of claim 10, further comprising:
 selectively activating the second magnetic nanoparticle by applying a third magnetic field having the second resonance frequency to the first and second magnetic nanoparticles.

12. A magnetic nanoparticle that is selectively activated by the method of claim 1 and has a magnetic vortex structure, wherein the resonance frequency divided by an external magnetic field varies according to the size of the magnetic nanoparticle.

13. A magnetic nanoparticle that is selectively activated by the method of claim 10 and has a magnetic vortex structure, wherein the resonance frequency divided by an external magnetic field varies according to the size of the magnetic nanoparticle.

* * * * *